United States Patent
Safai et al.

(10) Patent No.: US 10,539,538 B2
(45) Date of Patent: Jan. 21, 2020

(54) LASER ULTRASOUND SYSTEM AND METHOD FOR INSPECTION OF A CONTOURED STRUCTURE

(71) Applicant: The Boeing Company, Chicago, IL (US)

(72) Inventors: Morteza Safai, Newcastle, WA (US); Gary E. Georgeson, Tacoma, WA (US)

(73) Assignee: The Boeing Company, Chicago, IL (US)

(*) Notice: Subject to any disclaimer, the term of this patent is extended or adjusted under 35 U.S.C. 154(b) by 317 days.

(21) Appl. No.: 14/795,467

(22) Filed: Jul. 9, 2015

(65) Prior Publication Data

US 2017/0010242 A1   Jan. 12, 2017

(51) Int. Cl.
   *G01N 29/24*      (2006.01)
   *G01D 5/26*       (2006.01)

(52) U.S. Cl.
   CPC ......... *G01N 29/2418* (2013.01); *G01D 5/268* (2013.01)

(58) Field of Classification Search
   CPC .. G01D 5/268; G01N 29/043; G01N 21/1702; G01N 29/2418; G01N 2291/0231; G01N 2291/0258; B82Y 30/00
   USPC ...................................... 73/643, 655; 3/643
   See application file for complete search history.

(56) References Cited

U.S. PATENT DOCUMENTS

| | | | |
|---|---|---|---|
| 6,254,703 B1 | 7/2001 | Sokol et al. | |
| 7,500,953 B2* | 3/2009 | Oraevsky | A61B 5/0095 367/87 |
| 8,220,530 B2* | 7/2012 | Cola | B01J 23/745 165/133 |
| 9,401,135 B2* | 7/2016 | Davis | G01N 29/28 |
| 2006/0253942 A1* | 11/2006 | Barrera | B82Y 15/00 73/661 |
| 2012/0301663 A1* | 11/2012 | Koike | B82Y 30/00 428/114 |

(Continued)

FOREIGN PATENT DOCUMENTS

| | | | |
|---|---|---|---|
| CN | 105910989 | * | 8/2016 |
| WO | 2012112890 | | 8/2012 |

OTHER PUBLICATIONS

European Search Report, EP Application No. 16173575.8, dated Dec. 1, 2016.

(Continued)

*Primary Examiner* — Nimeshkumar D Patel
*Assistant Examiner* — Nashmiya S Fayyaz
(74) *Attorney, Agent, or Firm* — Perman & Green, LLP

(57) ABSTRACT

A method including ultrasonically scanning a structure with a laser ultrasound testing system where the structure is provided with an array of nanoscopic structures, the nanoscopic structures having a predetermined directional orientation, the nanoscopic structures disposed on a scanned surface of the structure, and determining if the structure meets a predetermined threshold. Aspects of this invention apply certain high emissivity coatings to structures for the purpose of significant improvement laser ultrasound inspection of those structures. The nanotechnology-based material in the coatings rapidly draws heat away, for maximum laser energy absorption while preventing surface heat damage to the composite surface from the laser beam.

20 Claims, 6 Drawing Sheets

(56) References Cited

U.S. PATENT DOCUMENTS

| | | | |
|---|---|---|---|
| 2013/0303909 A1* | 11/2013 | Kang | A61B 5/0095 |
| | | | 600/443 |
| 2013/0338504 A1* | 12/2013 | Demos | A61B 5/0097 |
| | | | 600/443 |
| 2014/0116146 A1 | 5/2014 | Bossi et al. | |
| 2015/0071324 A1* | 3/2015 | Lenczowski | G01N 25/72 |
| | | | 374/45 |
| 2018/0155854 A1* | 6/2018 | Cola | H01L 23/373 |

OTHER PUBLICATIONS

Grudzinskaya, et al. "Optoacoustic Effect in Dense Layers of Oriented Carbon Nanotubes: Its Use for Measuring the Optical Absorption Coefficient and the Film Thickness".Pleiades Publishing, Inc. Acoustic Physics, vol. 52, No. 3, pp. 274-277, 2006. DOI: 10.1134/S1063771006030067.

McKie, et al. "Rapid Inspection of Composites Using Laser-Based Ultrasound", Review of Progress in Quantitative Nondestructive Evaluation, vol. 12, edited by D.O. Thompson and D.E. Chimenti, Plenum Press, NY 1993, pp. 507-516.

\* cited by examiner

LASER ULTRASOUND SYSTEM AND METHOD FOR INSPECTION OF A CONTOURED STRUCTURE

BACKGROUND

A composite structure, as used herein, may be any structure comprised of at least one composite material. The composite material may include a matrix material and a reinforcement material. Composite structures may be inspected using different types of testing systems. A laser ultrasound testing system is an example of one type of testing system that may be used to non-destructively evaluate or inspect a composite structure for undesired inconsistencies. Laser ultrasound testing allows a composite structure to be tested without the testing system physically contacting the composite structure.

Laser ultrasound testing is a rapid, non-contact, non-couplant alternative to traditional ultrasound testing. Laser ultrasound testing may be used to inspect composite structures having complex contours such as those structures found in, for example, the aerospace industry. High power laser ultrasound testing systems have shown distinct benefits over conventional ultrasound testing but are very expensive and have a large footprint which requires significant floor space. Low power, high repetition rate, fiber-based ultrasound testing systems are being developed and have a distinct advantage of costing less than high power laser ultrasound testing systems. However, the low power laser ultrasound testing systems have limits as to how much energy can be input to the composite or other structures being tested, limiting the signal to noise ratio and depth of penetration.

Existing solutions for increasing the signal to noise ratio with laser ultrasound testing is averaging. For example, the signal to noise ratio of a laser ultrasound testing system can be improved, so that smaller inconsistencies can be found, by averaging multiple laser pulses at an inspection point. However, averaging the multiple laser pulses considerably slows down the scanning process. Further, overuse of averaging may generate excessive heat within the composite structure. For example, sustained laser pulses at one location increases the temperature of the composite structure at the laser impingement point. Improving the power density by focusing the laser spot can generate a strong stress pulse and improve the depth of penetration of incident energy within the composite structure however, focusing the laser spot may also generate excessive heat within the composite structure.

SUMMARY

Accordingly, apparatus and method, intended to address the above-identified concerns, would find utility.

One example of the present disclosure relates to a method comprising: ultrasonically scanning a structure with a laser ultrasound testing system where the structure is provided with an array of nanoscopic structures, the nanoscopic structures having a predetermined directional orientation, the nanoscopic structures disposed on a scanned surface of the structure; and determining if the structure meets a predetermined threshold.

One example of the present disclosure relates to a method comprising: disposing a nanotube array on at least a portion of a structure; directing incident energy of a laser ultrasound testing system into the structure with the nanotube array and generating a scan of the structure; and determining if the structure meets a predetermined threshold.

One example of the present disclosure relates to a method comprising: providing a laser ultrasound testing system; providing a structure having an array of nanoscopic structures, the nanoscopic structures having a predetermined directional orientation, the nanoscopic structures disposed on at least a portion of the structure; directing incident energy from the laser ultrasound testing system into the portion of the structure on which the array of nanoscopic structures is disposed; generating a scan of the structure; and determining if the structure meets a predetermined threshold.

One example of the present disclosure related to a non-destructive evaluation system comprising: a nanoscopic structure generation module configured to generate an array of nanoscopic structures on a surface of a structure to be evaluated such that the array of nanoscopic structures has a predetermined directional orientation; and an ultrasonic testing system configured to direct incident energy into the structure to be evaluated through the array of nanoscopic structures in a predetermined direction defined by the predetermined directional orientation of the array of nanoscopic structures.

BRIEF DESCRIPTION OF THE DRAWINGS

Figure 1:
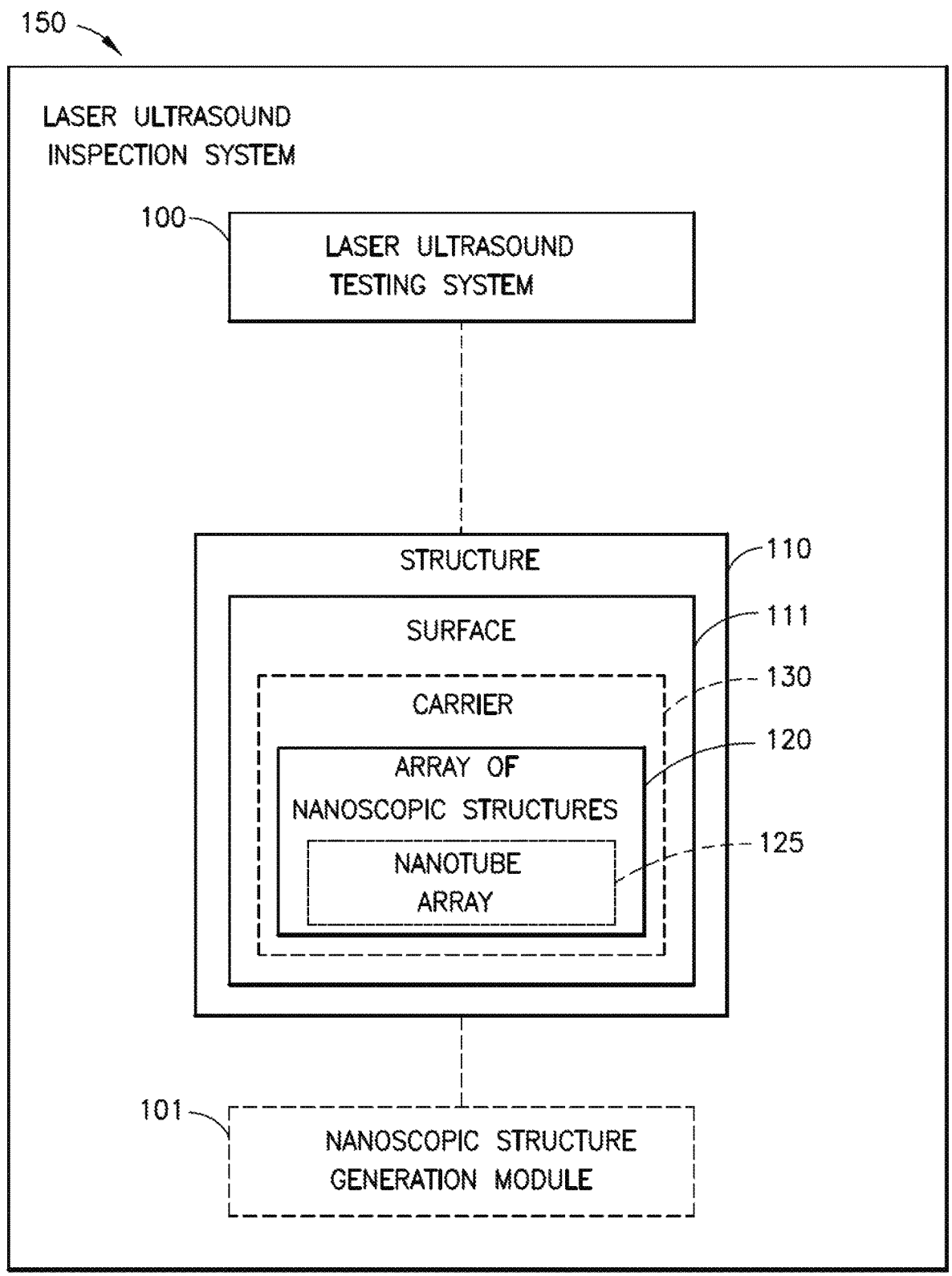
Figure 2A:
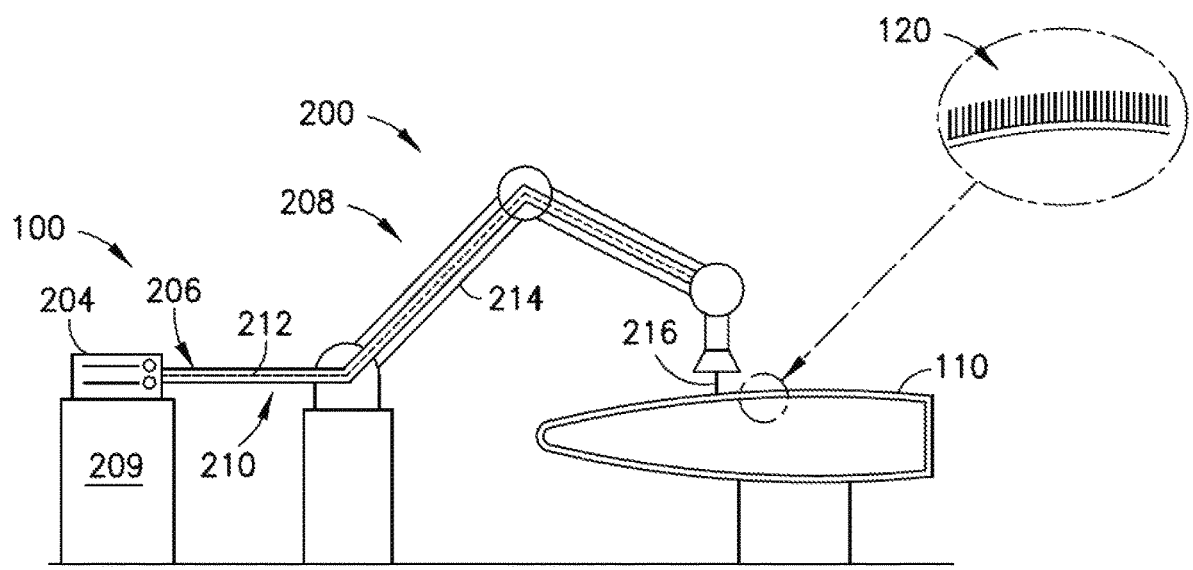
Figure 2B:
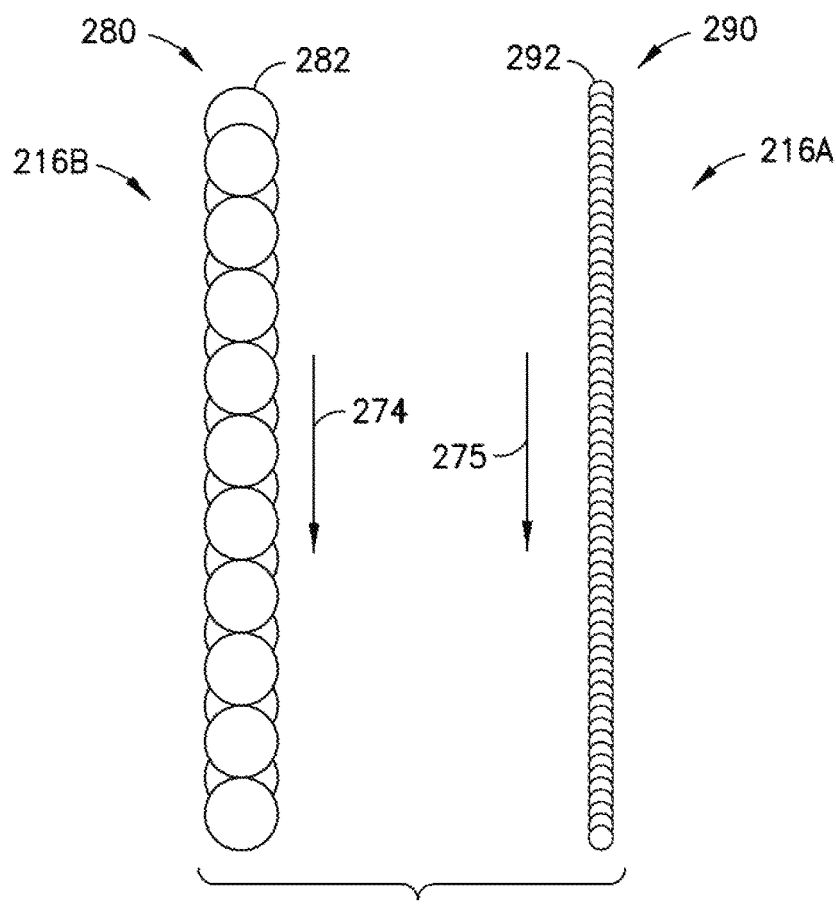
Figure 3:
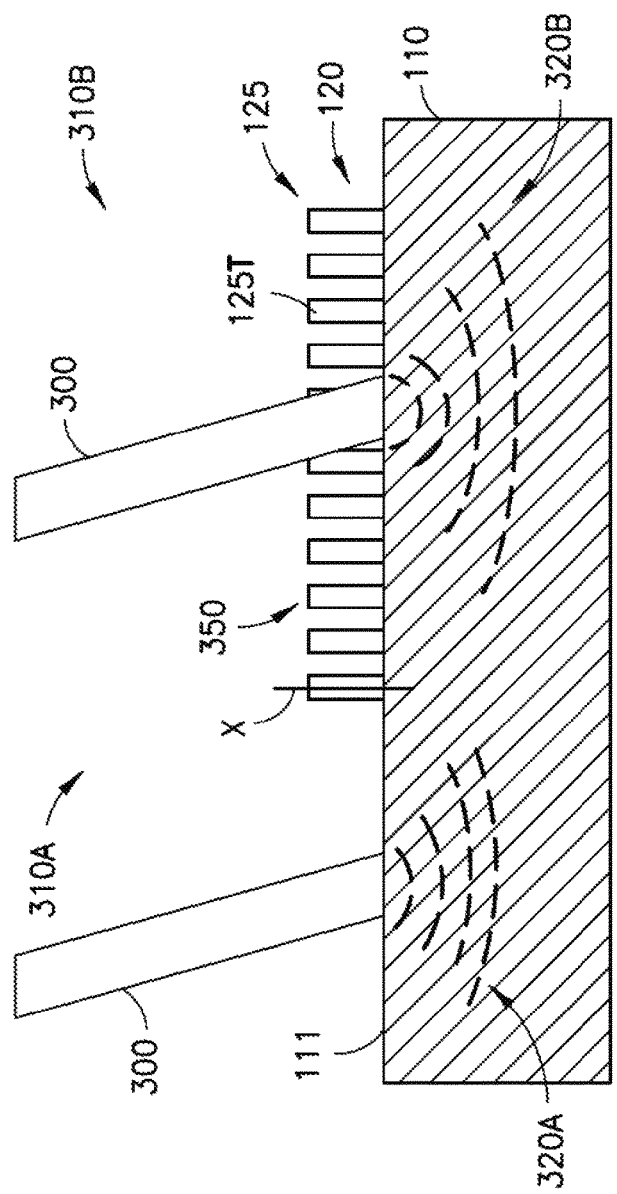
Figure 4:
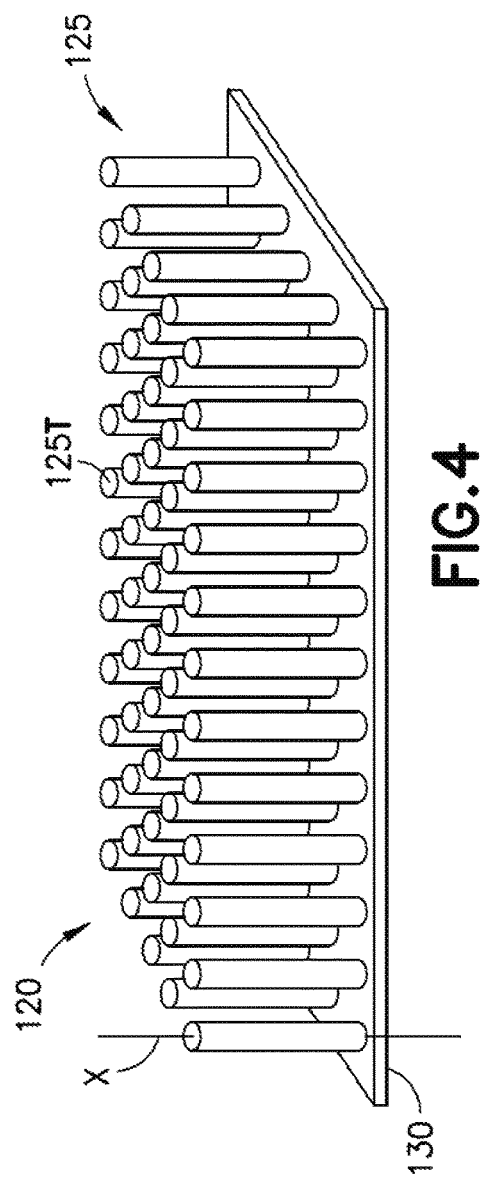
Figure 5:
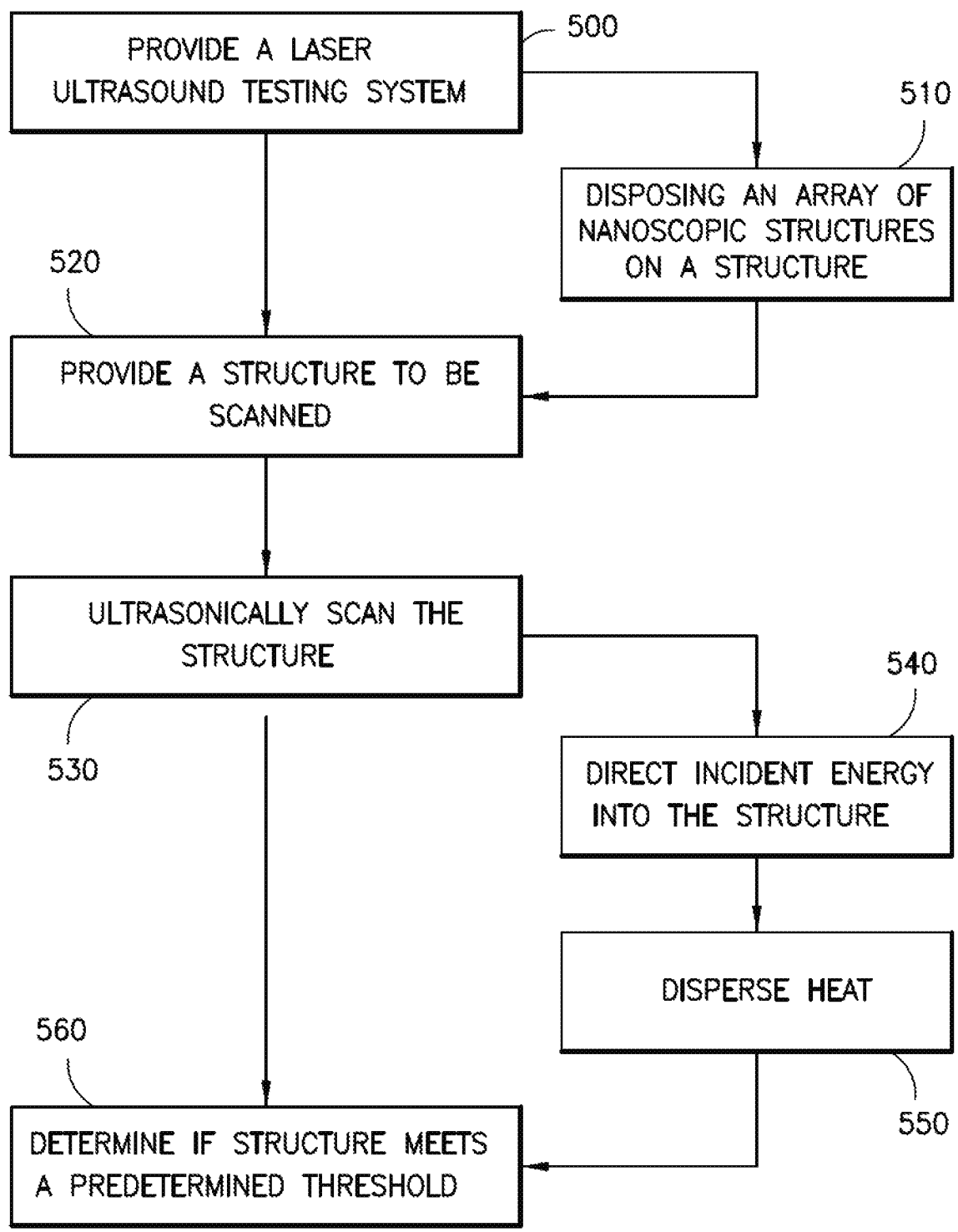
Figure 6:
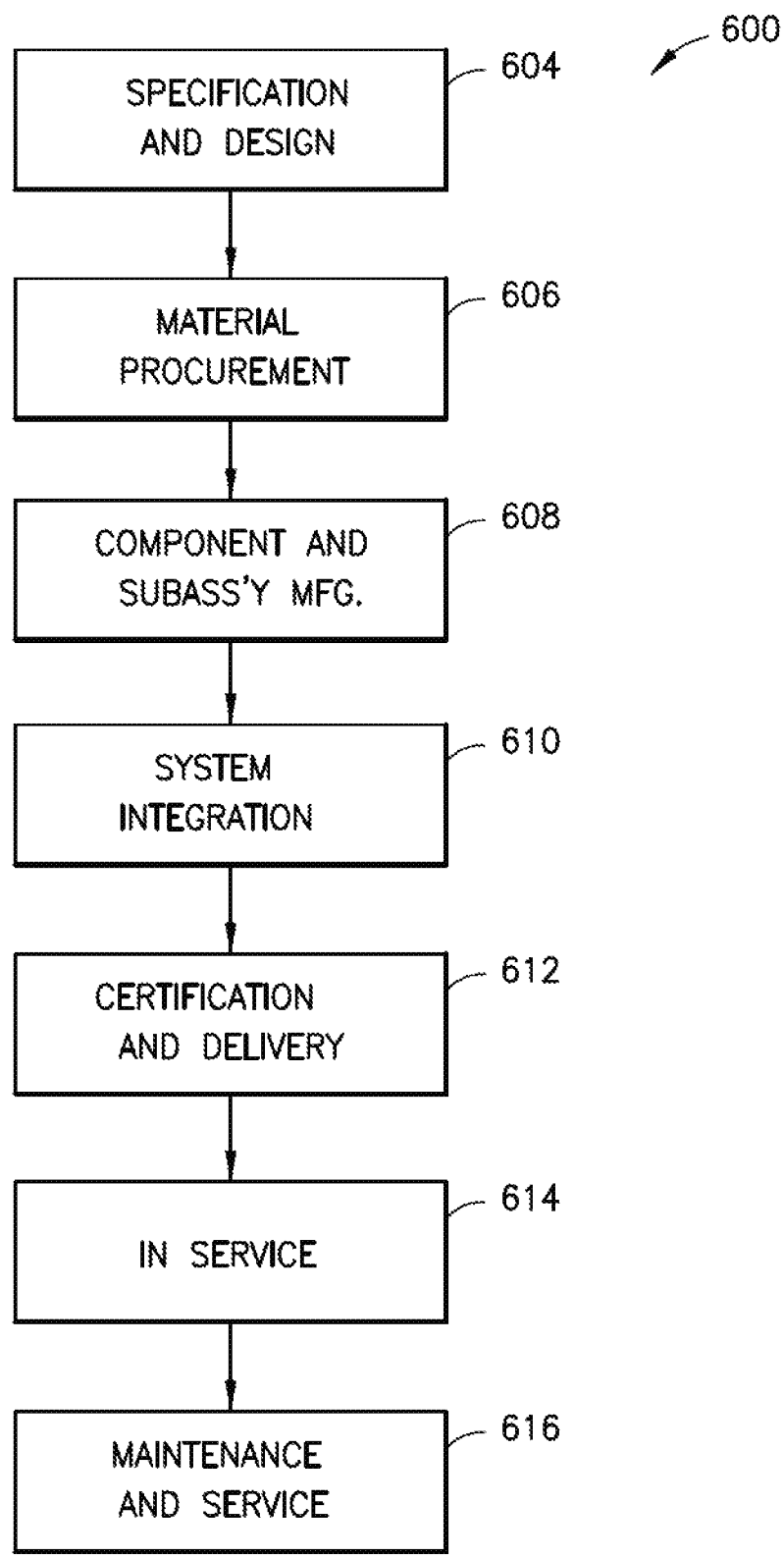

Having thus described examples of the disclosure in general terms, reference will now be made to the accompanying drawings, which are not necessarily drawn to scale, and wherein like reference characters designate the same or similar parts throughout the several views, and wherein:

FIG. 1 is a block diagram of an inspection system, according to aspects of the present disclosure;

FIG. 2A is a schematic illustration of a laser ultrasound testing system in accordance with aspects of the present disclosure;

FIG. 2B is a schematic illustration of two pulsed laser beams, according to aspects of the present disclosure;

FIG. 3 is a schematic illustration of laser ultrasound testing including an array of nanoscopic structures in accordance with aspects of the present disclosure;

FIG. 4 is a schematic illustration of an array of nanoscopic structures in accordance with aspects of the present disclosure;

FIG. 5 is a flow diagram of a method in accordance with aspects of the present disclosure;

FIG. 6 is a flow diagram of aircraft production and service methodology; and

Figure 7:
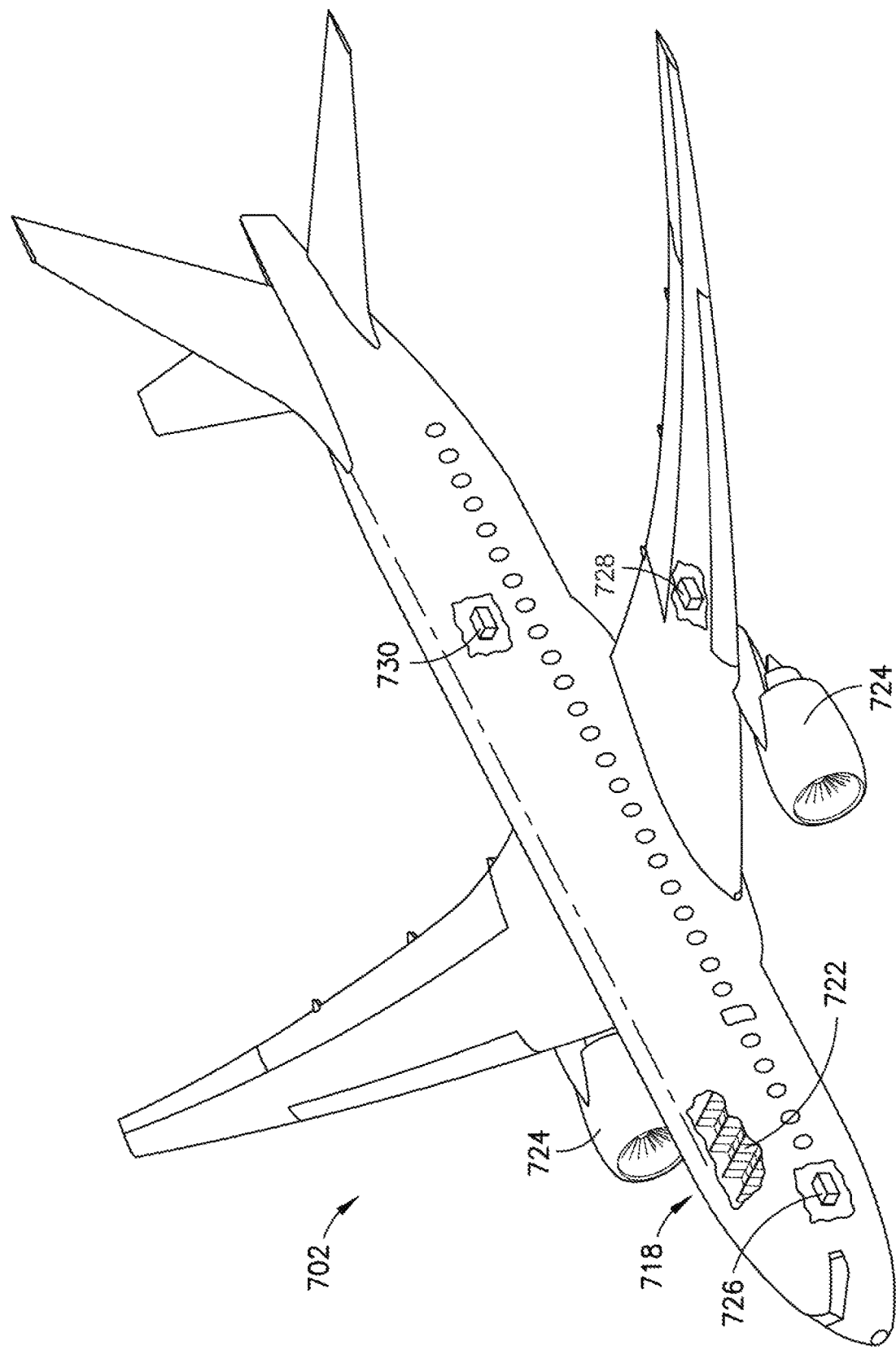

FIG. 7 is a schematic illustration of an aircraft including distributed vehicle systems.

In the block diagram(s) referred to above, solid lines, if any, connecting various elements and/or components may represent mechanical, electrical, fluid, optical, electromagnetic and other couplings and/or combinations thereof. As used herein, "coupled" means associated directly as well as indirectly. For example, a member A may be directly associated with a member B, or may be indirectly associated therewith, e.g., via another member C. Couplings other than those depicted in the block diagrams may also exist. Dashed lines, if any, connecting the various elements and/or components represent couplings similar in function and purpose to those represented by solid lines; however, couplings represented by the dashed lines may either be selectively provided or may relate to alternative or optional aspects of the disclosure. Likewise, elements and/or components, if any, represented with dashed lines, indicate alternative or optional aspects of the disclosure. Environmental elements, if any, are represented with dotted lines.

In the block diagram(s) referred to above, the blocks may also represent operations and/or portions thereof. Lines connecting the various blocks do not imply any particular order or dependency of the operations or portions thereof.

DETAILED DESCRIPTION

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

Reference herein to "one example" or "one aspect" means that one or more feature, structure, or characteristic described in connection with the example or aspect is included in at least one implementation. The phrase "one example" or "one aspect" in various places in the specification may or may not be referring to the same example or aspect.

Unless otherwise indicated, the terms "first," "second," "third," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Referring to FIGS. 1, 3 and 4, the aspects of the present disclosure apply certain high emissivity coatings 350 or carriers 130 to structures 110, such as composite structures and non-composite structures, for improving a signal to noise ratio of laser ultrasound inspection of those structures 110. In one aspect the high emissivity coatings 350 or carriers 130 include nanotechnology based materials to provide maximum laser energy absorption into the structure while preventing excessive heat build-up, from the laser beam, at the surface 111 of or within the structure 110. In one aspect the nanotechnology based materials form a laser energy absorber and heat dissipater that allow for improved inspection/scanning capabilities of the structures 110 over conventional laser ultrasound inspection methods.

Referring to FIGS. 1 and 2A, in one aspect a non-destructive evaluation system, such as laser ultrasound inspection system 150 includes a laser ultrasound testing system 100 and an array of nanoscopic structures 120 disposed on at least a portion of a surface 111 of a structure 110 to be tested/scanned. A nanoscopic structure generation module 101 may also be provided and be configured to form the array of nanoscopic structures 120 on the surface 111 of the structure 110. One example, of a laser ultrasound testing system 100 can be found in, for example, U.S. patent application Ser. No. 13/663,855 filed on Oct. 30, 2012 (now U.S. Pat. No. 9,625,423 issued on Apr. 18, 2017) the disclosure of which is incorporated by reference herein in its entirety. In one aspect, the laser ultrasound testing system 100 includes generation laser system 204, transmission system 206, and movement system 208. In one aspect the generation laser system 204 is mounted onto platform 209. Generation laser system 204 is configured to generate a pulsed laser beam that is carried through the transmission system 206, which in one aspect is a fiber optic transmission system 210. In one aspect the fiber optic transmission system 210 includes number of optical fibers 212 configured to carry a pulsed laser beam. In one aspect, the movement system 208 takes the form of robotic arm 214 while in other aspects the movement system 208 may be in the form of a gantry system configured to move the pulsed laser beam emitted from the transmission system 206. The robotic arm 214 is, in one aspect configured to move such that the pulsed laser beam emitted from transmission system 206 may be directed in different directions and in different locations of the structure 110. In one aspect the generation laser system 204 may generate a pulsed laser beam that is transmitted through the transmission system 206 and emitted from the transmission system 206 as pulsed laser beam 216. In one aspect the robotic arm 214 is configured to control the direction in which pulsed laser beam 216 is pointed and the movement of the pulsed laser beam 216 across the structure 110. In this manner, robotic arm 214 is configured to move such that pulsed laser beam 216 may be used to scan the structure 110.

In one aspect, using the fiber optic transmission system 210 to transmit and emit the pulsed laser beam 216 allows the laser ultrasound testing system 100 to be used in various types of environments. For example, a testing environment 200 in which the laser ultrasound inspection system 150 is located may be a room, an area around an assembly line, an area in a factory, an outdoor area, an area on top of a countertop surface, or some other type of environment. The pulsed laser beam 216 is generated and emitted in a manner that does not require testing environment 200 to have extensive shielding.

Generation laser system 204 is configured to generate pulsed laser beam 216 having number of properties in which each property in number of properties is within a selected range. The selected range for each property in the number of properties may be selected such that pulsed laser beam 216 is generated in a manner that causes a number of ultrasonic waves 320A, 320B to be formed in composite structure 110 when pulsed laser beam 216 encounters composite structure 110 without causing any undesired inconsistencies in composite structure 110 outside of selected tolerances. The number of properties may include for example, without limitation, pulse repetition rate, spot size, energy per pulse, absorption material, and/or other properties. Each of these properties may have values within selected ranges. The pulse repetition rate is the rate at which the pulses of laser energy are emitted to form pulsed laser beam 216. Pulse repetition rate may be described in terms of, for example, without limitation, frequency. In these illustrative examples, generation laser system 204 is configured to generate pulsed laser beam 216 such that pulsed laser beam 216 has pulse repetition rate between about 10,000 hertz (Hz) and about 500,000 hertz (Hz). A pulse repetition rate within this range may be considered a high pulse repetition rate. Further, the selected range for pulse repetition rate is selected such that pulse repetition rate is sufficiently high to allow the rate at which pulsed laser beam 216 is moved along composite structure 110 to be within selected tolerances. In particular, a high value for pulse repetition rate allows the rate at which pulse repetition rate scans composite structure 110 to be high as well. In other words, as pulse repetition rate increases, the scanning rate may also increase.

Spot size is the size of the area on the surface of composite structure 110 illuminated by pulsed laser beam 216. In these illustrative examples, generation laser system 204 is configured to generate pulsed laser beam 216 such that spot size is less than about 1 millimeter (mm). A spot size less than about 1 millimeter (mm) may be considered a small spot size in these examples. The selected range for spot size of pulsed laser beam 216 is selected such that the path formed by pulsed laser beam 216 as pulsed laser beam 216 scans composite structure 110 has a width that is sufficiently narrow to allow smaller features of composite structure 110 to be characterized.

Referring now to FIG. 2B, an illustration of two pulsed laser beams is depicted in accordance with aspects of the present disclosure. In this illustrative example, pulsed laser beam 290 is an example of one implementation for pulsed laser beam 216. Pulsed laser beam 290 forms spot 292. In one aspect the spot 292 has a spot size less than about 1 millimeter (mm). Pulsed laser beam 290 may be moved in the direction of arrow 275 to form beam path 216A. Pulsed laser beam 280 is another example of a pulsed laser beam that may be formed using a generation laser system such as, for example, a laser system that uses a gas laser source. Pulsed laser beam 280 forms spot 282. In one aspect the spot 282 has a spot size that is about 5 millimeters (mm). Pulsed laser beam 280 may be moved in the direction of arrow 274 to form beam path 216B. As depicted, beam path 216A is narrower than beam path 216B. In one aspect, the data that may be generated using beam path 216A allows a finer level of detail to be characterized than the data that may be generated using beam path 216B.

In one aspect the laser ultrasound testing system 100 is a low power testing system where the pulsed laser beam is transmitted over a fiber optic transmission, as described above. For example, energy per pulse may be the amount of energy contained within each pulse of laser energy that forms pulsed laser beam 216. The pulsed laser beam 121 is generated such that energy per pulse is within a range that is selected to allow the number of ultrasonic waves 320A, 320B (see FIG. 3) to be formed in the structure 110 without causing a number of inconsistencies in the composite structure 110 outside of selected tolerances. In one aspect, generation laser system 204 is configured to generate the pulsed laser beam 216 such that the energy per pulse is a low power energy pulse within the range of about 1 microjoule ($\mu J$) to about 10,000 microjoules ($\mu J$). In one aspect, the combination of a laser beam spot size and energy per pulse may be used to produce an optical fluence within a desired range. As used herein, "fluence" may be the energy transferred through a unit area. The pulsed laser beam 216 may be generated such that the optical fluence per pulse ranges between about 0.1 millijoules per centimeters squared ($mJ/cm^2$) to about 1000 millijoules per centimeters squared ($mJ/cm^2$). The value within this range selected for the optical fluence per pulse may be selected such that pulsed laser beam 216 does not cause any inconsistencies on and/or in structure 110 outside of selected tolerances. In other aspects, the laser ultrasound testing system 100 is a high power testing system where the energy per pulse is greater than about 10,000 microjoules ($\mu J$).

Referring to FIGS. 1, 3 and 4, as described above, an array of nanoscopic structures 120 having a high emissivity, such as for example an emissivity as close to 1 as possible, is disposed on at least a portion of the surface 111 of the structure 110. In one aspect the array of nanoscopic structures 120 includes a nanotube array 125 however, in other aspects the nanostructures forming the array of nanoscopic structures may have any shape and/or configuration that provides for energy absorption into the structure 110 and/or heat dissipation from the structure 110. In one aspect the nanotube array 125 is a carbon nanotube array. While carbon is used as an example of a material used to construct nanostructures of the array of nanoscopic structures 120 in other aspects other materials with a high emissivity are used including, but not limited to, ceramics and polymer-silicates.

In one aspect, the array of nanoscopic structures 120 is formed or deposited directly on the surface 111 of the structure 110 to form the high emissivity coating 350 on the surface 111. The array of nanoscopic structures 120 is formed or deposited on the surface 111 by the nanoscopic structure generation module 101 such as by, for example, arc discharge, laser ablation, chemical vapor deposition, plasma enhanced chemical vapor deposition, and/or Ultrasound Atomization. The nanoscopic structure, such as the carbon nanotubes 125T, form a thin layer on the surface 111 having any suitable thickness (e.g. on the order of a few microns) that allows the nanoscopic structure to direct energy, such as for example, about 80% to about 90% of laser energy, into the structure 110 as described herein. In other aspects, the nanoscopic structure directs more than about 90% or less than about 80% of the laser energy into the structure 110. In one aspect, the nanoscopic structure, such as the carbon nanotubes 125T, are oriented so that a lengthwise axis X of each nanotube is substantially perpendicular to the surface 111. In another aspect, the nanoscopic structure, such as the carbon nanotubes 125T, are oriented in a forest type of layer where a majority of the nanoscopic structure is aligned substantially perpendicular to the surface 111. In still other aspects, the nanoscopic structures have any suitable arrangement that, again, allows the nanoscopic structure to direct energy into the structure 110 as described herein. Where the structure 110 is a composite structure, the array of nanoscopic structures 120 is formed on the surface 111, for example, during or after the composite curing process.

In one aspect, the array of nanoscopic structures 120 is formed or deposited on a carrier 130 where the carrier is affixed to the surface 111 of the structure 110. The array of nanoscopic structures 120 is formed or deposited on the carrier 130 by the nanoscopic structure generation module 101 such as by, for example, arc discharge, laser ablation, chemical vapor deposition, plasma enhanced chemical vapor deposition, and/or pyrolysis (e.g. liquid, solid or flame). The nanoscopic structure, such as the carbon nanotubes 125T, form a thin layer or coating on the carrier 130 having any suitable thickness (e.g. on the order of a few microns) that allows the nanoscopic structure to direct energy, such as for example, about 80% to about 90% of laser energy, into the structure 110 as described herein. In other aspects, the nanoscopic structure directs more than about 90% or less than about 80% of the laser energy into the structure 110. In one aspect, the nanoscopic structure, such as the carbon nanotubes 125T, are oriented so that a lengthwise axis X of each nanotube is substantially perpendicular to the surface 111. In another aspect, the nanoscopic structure, such as the carbon nanotubes 125T, are oriented in a forest type of layer where a majority of the nanoscopic structure is aligned substantially perpendicular to the surface 111. In still other aspects, the nanoscopic structures have any suitable arrangement that, again, allows the nanoscopic structure to direct energy into the structure 110 as described herein. Where the structure 110 is a composite structure, the carrier 130 including the array of nanoscopic structures 120 is affixed to the surface 111, for example, during or after the composite curing process. In one aspect the carrier 130 is any suitable carrier such as a film that is adhered or otherwise fastened to the surface in any manner that, for example, allows for the removal of the carrier 130. In other aspects, the carrier may remain on the structure 110.

As can be seen in FIG. 3 about 100% of incident energy 300 from the pulsed laser beam 216 is directed toward the surface 111 of the structure 110. Where, for example, the incident energy 300 is directed to a portion of the surface 111 lacking the array of nanoscopic structures 120 about, for example, 20% of the incident energy is absorbed into the structure 110 forming ultrasonic waves 320A and about 80% of the incident energy is reflected as reflected energy 310A. In one aspect, as described above, where the incident energy 300 is directed to a portion of the surface that includes the array of nanoscopic structures 120 the directionality of the nanoscopic structures allows for directed transmission of fluence into the structure substantially without distortion of the structure 110 so that the spot size can be maintained with a predetermined pulse energy and so that heat is dissipated from the structure 110. In one aspect, the array of nanoscopic structures 120 allows for about, for example, 80% to about 90% of the incident energy is absorbed into the structure 110 forming ultrasonic waves 320B and about 20% to about 10% of the incident energy is reflected as reflected energy 310B. The ultrasonic waves 320B are stronger than (e.g. have greater energy) and travel further into the structure 110 with a greater depth of penetration than the ultrasonic waves 320A because of the increased energy directed into the structure by the array of nanoscopic structures 120. As a result of the increased energy directed into the structure 110, the signal to noise ratio with respect to the laser ultrasound testing/scanning is increased. In one aspect, the array of nanoscopic structures 120 allows for decreased spot sizes which allows for higher speed scans of the structure 110.

Referring now to FIGS. 1, 2, 3 and 5 an exemplary inspection/testing method will be described. In one aspect a laser ultrasound testing system 100 is provided (FIG. 5, Block 500). A structure 110 to be scanned is also provided (FIG. 5, Block 520). In one aspect, the structure 110 is provided having the array of nanoscopic structures 120 disposed on at least the portion of the structure 110, in the manner described herein, prior to testing (FIG. 5, Block 510). The structure is ultrasonically scanned with the laser ultrasound testing system 100 (FIG. 5, Block 530) such as by moving the pulsed laser beam across the surface 111 of the structure and detecting the ultrasonic waves reflected by the structure 110. In one aspect the incident energy 300 of the pulsed laser beam 216 is directed into the structure with the array of nanoscopic structures 120 (FIG. 5, Block 540) where the pulsed laser beam 216 generates ultrasonic waves 320B that propagate through and are reflected by the structure 110. As described above, the array of nanoscopic structures 120 forms an energy absorber and a thermal protection layer for the structure 110 where heat generated on or in the structure 110 by the pulsed laser beam 216 is dispersed by the array of nanoscopic structures 120 (FIG. 5, Block 550), which in one aspect allows for laser beam spots to be averaged for further increasing the signal to noise ratio useful in ultrasound inspection. A determination as to whether the structure 110 meets a predetermined threshold is made based on the ultrasonic scan (FIG. 5, Block 560). In one aspect, the predetermined threshold is a metrological threshold such as, for example, detecting inconsistencies within (e.g. internal structural consistency) and quality of the structure 110. In one aspect, the array of nanoscopic structures 120 and/or the carrier 130 is removed from the surface 111 of the structure after testing while in other aspects the array of nanoscopic structures 120 and/or the carrier 130 remains on the surface 111 of the structure 110 after testing.

The aspects of the present disclosure reduce the costs associated with non-contact, non-coupled ultrasonic inspection of complex structures, such as composite structures by allowing for the use of low power laser testing systems when performing non-destructive evaluation of the complex structures. The aspects of the present disclosure allow for the non-destructive evaluation of, for example, materials and structure with complex curvature or non-constant (e.g. variable) radii; materials and structures that cannot get wet; porosity of a structure disposed over a core; porosity of a face sheet; ply-counting; edges, cut-outs and holes; defect detection near bondlines and surfaces; composite wrinkle quantification; weld inspection; and layered material inspection.

The disclosure and drawing figures describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, in some aspects of the disclosure, not all operations described herein need be performed.

Examples of the disclosure may be described in the context of an aircraft manufacturing and service method 600 as shown in FIG. 6 and an aircraft 702 as shown in FIG. 7. During pre-production, illustrative method 600 may include specification and design 604 of the aircraft 702 and material procurement 606. During production, component and subassembly manufacturing 608 and system integration 610 of the aircraft 702 take place. Thereafter, the aircraft 702 may go through certification and delivery 612 to be placed in service 614. While in service by a customer, the aircraft 702 is scheduled for routine maintenance and service 616 (which may also include modification, reconfiguration, refurbishment, and so on).

Each of the processes of the illustrative method 600 may be performed or carried out by a system integrator, a third party, and/or an operator (e.g., a customer). For the purposes of this description, a system integrator may include, without limitation, any number of aircraft manufacturers and major-system subcontractors; a third party may include, without limitation, any number of vendors, subcontractors, and suppliers; and an operator may be an airline, leasing company, military entity, service organization, and so on.

As shown in FIG. 7, the aircraft 702 produced by the illustrative method 600 may include an airframe 718 with a plurality of high-level systems and an interior 722. Examples of high-level systems, which are distributed throughout the aircraft, include one or more of a propulsion system 724, an electrical power system 726, a hydraulic system 728, and an environmental system 730. Any number of other systems may be included. Although an aerospace example is shown, the principles of the invention may be applied to other industries, such as the automotive and maritime industries.

Apparatus and methods shown or described herein may be employed during any one or more of the stages of the manufacturing and service method 600. For example, components or subassemblies corresponding to component and subassembly manufacturing 608 may be fabricated or manufactured in a manner similar to components or subassemblies produced while the aircraft 702 is in service. Also, one or more aspects of the apparatus, method, or combination thereof may be utilized during the production states 608 and 610, for example, by substantially expediting assembly of or reducing the cost of an aircraft 702. Similarly, one or more aspects of the apparatus or method realizations, or a combination thereof, may be utilized, for example and without limitation, while the aircraft 702 is in service, e.g., operation, maintenance and service 616.

Different examples and aspects of the apparatus and methods are disclosed herein that include a variety of components, features, and functionality. It should be understood that the various examples and aspects of the apparatus and methods disclosed herein may include any of the components, features, and functionality of any of the other examples and aspects of the apparatus and methods disclosed herein in any combination, and all of such possibilities are intended to be within the spirit and scope of the present disclosure.

Many modifications and other examples of the disclosure set forth herein will come to mind to one skilled in the art to which the disclosure pertains having the benefit of the teachings presented in the foregoing descriptions and the associated drawings.

In one or more aspects of the present disclosure a method includes ultrasonically scanning a structure with a laser ultrasound testing system where the structure is provided with an array of nanoscopic structures, the nanoscopic structures having a predetermined directional orientation, the nanoscopic structures disposed on a scanned surface of the structure; and determining if the structure meets a predetermined threshold.

In one or more aspects of the present disclosure the method further comprising directing incident energy from the laser ultrasound testing system into the structure using the array of nanoscopic structures.

In one or more aspects of the present disclosure the array of nanoscopic structures comprise a nanotube coating, the method further comprising directing incident energy from the laser ultrasound testing system into the structure using the nanotube coating.

In one or more aspects of the present disclosure the nanotube coating includes nanotubes arranged substantially perpendicular to the scanned surface of the structure.

In one or more aspects of the present disclosure the method further comprising dispersing heat generated by the laser ultrasound testing system on the structure.

In one or more aspects of the present disclosure the laser ultrasound testing system is a low power fiber-based laser system.

In one or more aspects of the present disclosure the method further comprising coating the scanned surface with the array of nanoscopic structures.

In one or more aspects of the present disclosure a method includes disposing a nanotube array on at least a portion of a structure; directing incident energy of a laser ultrasound testing system into the structure with the nanotube array and generating a scan of the structure; and determining if the structure meets a predetermined threshold.

In one or more aspects of the present disclosure the nanotube array includes nanotubes arranged substantially perpendicular to the portion of the structure.

In one or more aspects of the present disclosure the nanotube array is disposed on a carrier and the carrier is affixed to the portion of the structure.

In one or more aspects of the present disclosure the laser ultrasound testing system is a low power fiber-based laser system.

In one or more aspects of the present disclosure the method further comprising dispersing heat generated by the laser ultrasound testing system on the structure with the nanotube array.

In one or more aspects of the present disclosure a method includes providing a laser ultrasound testing system; providing a structure having an array of nanoscopic structures, the nanoscopic structures having a predetermined directional orientation, the nanoscopic structures disposed on at least a portion of the structure; directing incident energy from the laser ultrasound testing system into the portion of the structure on which the array of nanoscopic structures is disposed; generating a scan of the structure; and determining if the structure meets a predetermined threshold.

In one or more aspects of the present disclosure the array of nanoscopic structures comprise a nanotube coating, the method further comprising directing incident energy from the laser ultrasound testing system into the structure with the nanotube coating.

In one or more aspects of the present disclosure the nanotube coating includes nanotubes arranged substantially perpendicular to the portion of the structure.

In one or more aspects of the present disclosure the nanotube coating includes nanotubes having a forest arrangement.

In one or more aspects of the present disclosure the method further comprising dispersing heat generated by the laser ultrasound testing system on the structure.

In one or more aspects of the present disclosure the laser ultrasound testing system is a low power fiber-based laser system.

In one or more aspects of the present disclosure providing the structure having the array of nanoscopic structures disposed on at least the portion of the structure includes coating the scanned surface with the array of nanoscopic structures.

In one or more aspects of the present disclosure providing the structure having the array of nanoscopic structures disposed on at least the portion of the structure includes placing a carrier on the portion of the structure where the array of nanoscopic structures is integrated with the carrier.

In one or more aspects of the present disclosure a non-destructive evaluation system includes a nanoscopic structure generation module configured to generate an array of nanoscopic structures on a surface of a structure to be evaluated such that the array of nanoscopic structures has a predetermined directional orientation; and an ultrasonic testing system configured to direct incident energy into the structure to be evaluated through the array of nanoscopic structures in a predetermined direction defined by the predetermined directional orientation of the array of nanoscopic structures.

In one or more aspects of the present disclosure the ultrasonic testing system comprises a laser ultrasound testing system.

In one or more aspects of the present disclosure the ultrasonic testing system comprises a low power fiber-based laser system.

In one or more aspects of the present disclosure the nanoscopic structure generation module is configured to generate the array of nanoscopic structures so that nanoscopic structures of the array of nanoscopic structures are arranged substantially perpendicular to the surface.

In one or more aspects of the present disclosure the array of nanoscopic structures comprises nanotubes.

Therefore, it is to be understood that the disclosure is not to be limited to the specific embodiments disclosed and that modifications and other embodiments are intended to be included within the scope of the appended claims. Moreover, although the foregoing descriptions and the associated drawings describe example embodiments in the context of certain illustrative combinations of elements and/or functions, it should be appreciated that different combinations of elements and/or functions may be provided by alternative implementations without departing from the scope of the appended claims.

What is claimed is:

1. A method comprising:
ultrasonically scanning a structure with a laser ultrasound testing system by moving a pulsed laser beam across a surface of the structure and detecting ultrasonic waves reflected by the structure, where the structure is provided with an array of nanoscopic structures, the nanoscopic structures having a predetermined directional orientation relative to the structure, where the nanoscopic structures are deposited directly on a scanned surface of the structure by a nanoscopic structure generation module so as to be integrally formed on and depend from, so as to be stationarily fixed to and form a unitary member with, the scanned surface of the structure so that a free end of a respective nanoscopic structure extends from the scanned surface of the structure in the predetermined directional orientation; and
determining, based on ultrasonic scanning of the structure with the laser ultrasound testing system, if the structure meets a predetermined threshold.

2. The method of claim 1, further comprising directing incident energy from the laser ultrasound testing system into the structure using the array of nanoscopic structures.

3. The method of claim 1, wherein the array of nanoscopic structures comprise a nanotube coating, the method further comprising directing incident energy from the laser ultrasound testing system into the structure using the nanotube coating.

4. The method of claim 3, wherein the nanotube coating includes nanotubes arranged substantially perpendicular to the scanned surface of the structure.

5. The method of claim 1, further comprising dispersing, with the nanoscopic structures, heat generated by the laser ultrasound testing system on the structure.

6. The method of claim 1, wherein the laser ultrasound testing system is a low power fiber-based laser system.

7. The method of claim 1, further comprising coating the scanned surface with the array of nanoscopic structures.

8. A method comprising:
disposing a nanotube array on at least a portion of a structure, where the nanotube array is integrally formed on a carrier film by a nanoscopic structure generation module so as to be fixed to and form a unitary member with the carrier film, and the carrier film is affixed to the portion of the structure so that the nanotube array extends away from, so as to be stationarily fixed relative to, the structure;
directing incident energy of a laser ultrasound testing system into the structure in a predetermined direction with the nanotube array and generating a scan of the structure, where the nanotube array includes nanoscopic structures that have respective free ends arranged relative to a surface of the structure so as to extend from the structure and define the predetermined direction, and a pulsed laser beam of the laser ultrasound testing system is moved across the surface of the structure and ultrasonic waves reflected by the structure are detected; and
determining, with the laser ultrasound testing system, if the structure meets a predetermined threshold.

9. The method of claim 8, wherein the nanotube array includes nanotubes arranged substantially perpendicular to the portion of the structure.

10. The method of claim 8, wherein the laser ultrasound testing system is a low power fiber-based laser system.

11. The method of claim 8, further comprising dispersing heat generated by the laser ultrasound testing system on the structure with the nanotube array.

12. A non-destructive evaluation system comprising:
a nanoscopic structure generation module configured to generate an array of nanoscopic structures on a surface of a structure to be evaluated such that nanoscopic structures of the array of nanoscopic structures are formed directly on the structure or on a carrier film that is affixed to the structure so that the nanoscopic structures are integrally formed on the structure or the carrier film that is affixed to the structure and depend from, so as to be stationarily fixed to and form a unitary member with, the structure or the carrier film that is affixed to the structure and respective free ends of the nanoscopic structures of the array of nanoscopic structures extend from the surface in a predetermined directional orientation; and
a laser ultrasound testing system configured to direct incident energy into the structure to be evaluated through the array of nanoscopic structures so that a configuration of the array of nanoscopic structures is configured to direct the incident energy into the structure in a predetermined direction defined by the predetermined directional orientation of the array of nanoscopic structures, and a pulsed laser beam of the laser ultrasound testing system is moved across the surface of the structure and ultrasonic waves reflected by the structure are detected.

13. The non-destructive evaluation system of claim 12, wherein the laser ultrasound testing system comprises a low power fiber-based laser system.

14. The non-destructive evaluation system of claim 12, wherein the nanoscopic structure generation module is configured to generate the array of nanoscopic structures so that nanoscopic structures of the array of nanoscopic structures are arranged substantially perpendicular to the surface.

15. The non-destructive evaluation system of claim 12, wherein the array of nanoscopic structures comprises nanotubes.

16. The method of claim 1, wherein the nanoscopic structures disposed on a scanned surface of the structure so as to increase, compared to ultrasonically scanning the structure without the nanoscopic structures disposed on a scanned surface of the structure, a signal to noise ratio when ultrasonically scanning the structure.

17. The method of claim 1, wherein the nanoscopic structures direct about 80% to about 90% of laser energy from the laser ultrasound testing machine into the structure.

18. The method of claim 1, wherein the structure is a composite structure.

19. The method of claim 1, wherein the scanned surface comprises a surface of an aircraft.

20. The system of claim 12, wherein the structure is a composite structure of an aircraft.

* * * * *